(12) United States Patent  
Busch et al.

(10) Patent No.: US 8,573,200 B2  
(45) Date of Patent: Nov. 5, 2013

(54) MAGNETIC COUPLING ASSEMBLY AND METHOD OF USING SAME

(75) Inventors: Lance Ranard Busch, Trafford, PA (US); Peter Chi Fai Ho, Pittsburgh, PA (US)

(73) Assignee: RIC Investments, LLC, Wilmington, DE (US)

( * ) Notice: Subject to any disclaimer, the term of this patent is extended or adjusted under 35 U.S.C. 154(b) by 580 days.

(21) Appl. No.: 12/857,616

(22) Filed: Aug. 17, 2010

(65) Prior Publication Data

US 2010/0307497 A1 Dec. 9, 2010

Related U.S. Application Data

(62) Division of application No. 11/726,904, filed on Mar. 23, 2007, now Pat. No. 7,793,987.

(60) Provisional application No. 60/785,431, filed on Mar. 24, 2006.

(51) Int. Cl.  
*A61M 11/00* (2006.01)

(52) U.S. Cl.  
USPC ...................................... 128/202.27; 285/9.1

(58) Field of Classification Search  
USPC ............ 285/9.1; 128/206.21, 207.11, 202.27, 128/206.24, 205.25, 200.24  
See application file for complete search history.

(56) References Cited

U.S. PATENT DOCUMENTS

| | | |
|---|---|---|
| 2,953,979 A | 9/1960 | Maynard |
| 3,181,895 A | 5/1965 | Cator |
| 3,582,017 A | 6/1971 | Zecca |
| 4,004,298 A | 1/1977 | Freed |
| 4,054,128 A | 10/1977 | Seufert |
| 5,096,230 A | 3/1992 | Pausch |
| 5,419,354 A | 5/1995 | Krynicki |
| 5,624,410 A | 4/1997 | Tsukada |
| 5,817,067 A | 10/1998 | Tsukada |
| 2005/0155604 A1* | 7/2005 | Ging et al. ............... 128/206.21 |

* cited by examiner

*Primary Examiner* — Steven Douglas  
(74) *Attorney, Agent, or Firm* — Michael W. Haas

(57) ABSTRACT

A magnetic coupling assembly for use in coupling portions of a gas deliver system. The magnetic coupling assembly includes a first member and a second member to be coupled together. The attractive forces between the first plurality of magnetic elements on the first member and a second plurality of magnetic elements on the second member join these member. The poles of magnetic elements in the first and second plurality of magnetic elements is opposite that of an adjacent magnetic element. The first and second members are easily detached from one another simply by rotating the first member relative to the second member such that the magnetic poles of the magnetic elements in each plurality of magnetic elements become unaligned, causing an weakening of the attractive forces.

15 Claims, 6 Drawing Sheets

MAGNETIC COUPLING ASSEMBLY AND METHOD OF USING SAME

CROSS-REFERENCE TO RELATED APPLICATIONS

This application is a Divisional under 35 U.S.C. §120/121 of U.S. patent application Ser. No. 11/726,904, filed Mar. 23, 2007, which claims priority under 35 U.S.C. §119(e) from provisional U.S. patent application No. 60/785,431, filed Mar. 24, 2006, the contents of which are incorporated herein by reference.

BACKGROUND OF THE INVENTION

1. Field of the Invention

The present invention relates to a magnetic coupling assembly for use in a gas flow delivery system, and, in particular, to a magnetic coupling assembly that includes at least two members each of which each includes a plurality of magnetic elements of alternating polarity to couple the two members together.

2. Description of the Related Art

Gas flow delivery systems are used to deliver a flow of gas to an airway of a subject. Such systems are typically used in the medical field to deliver gas to a patient. Examples of gas flow delivery systems in the medical field include a ventilator or respirator, which replaces or supplements a patient's respiration, and a pressure support system, which provides a flow of gas to an airway of a patient at an elevated pressure to treat a medical disorder, such as obstructive sleep apnea (OSA). Pressure support systems include, but are not limited to continuous positive airway pressure (CPAP) devices, which deliver a constant positive pressure to the airway of a patient over multiple respiratory cycles, and variable pressure devices, where the pressure of the flow of gas delivered to the patient is variable.

Variable pressure support devices include auto-titrating devices that are capable of changing a base pressure or pressure profile delivered to the patent based on a monitored condition of the patient. Other variable pressure devices change the pressure of the flow of gas during a respiratory cycle. These devices include the following: a proportional assist ventilation (PAV®), a proportional positive airway pressure (PPAP®) device, a C-Flex™ device, a Bi-Flex™ device, and a BiPAP® device manufactured and distributed by Respironics, Inc. of Pittsburgh, Pa. The BiPAP device is a bi-level pressure support system in which the pressure provided to the patient varies with the patient's respiratory cycle so that a higher pressure is delivered during inspiration than during expiration. For purposes of the present invention, all systems that deliver a flow of gas or pressurized gas to an airway of a subject are referred to as gas flow delivery systems.

A typical gas flow delivery system comprises a pressure/flow generating system that produces a flow of gas for delivery to a patient and a system for communicating the flow of gas to the patient. The latter system typically includes a flexible conduit having one end coupled to a pressure/flow generating device and a second end portion that couples to an airway of patient by means of a patient interface assembly worn by the patient. The conduit, which is also referred to as an air hose or patient circuit, carries the flow of gas from the pressure generating device during operation of the system. The patient interface assembly includes a patient interface device, typically in the form of a nasal, oral, or nasal/oral mask, and a headgear assembly that attaches to patient interface device to the user. The second end portion of the conduit is coupled to the patient interface device to communicate the flow of gas to the airway of the patient.

The components of the gas flow delivery system are coupled together such that they can be assembled and disassembled by the caregiver or user. For example, the mask is selectively coupled to the distal end of the patient circuit, and the pressure/flow generating device is selectively coupled to the proximal end of the patient circuit. In addition, the headgear assembly is selectively coupled to the patient interface device in the patient interface assembly.

In a conventional gas flow delivery system, mechanical forms of connections are used to join these various members to one another. For example, friction fittings are used to join the ends of the air hose to the patient interface assembly and the pressure/flow generating device. Clips, snaps, or hooks are used to join the headgear straps to the mask. While these techniques are suitable for the purpose of joining two components of the gas flow delivery system to one another, the present inventors recognized that they can be difficult to assemble and disassemble for users with impaired physical and/or mental ability.

SUMMARY OF THE INVENTION

Accordingly, it is an object of the present invention to provide a technique for coupling components of a gas flow delivery system that overcomes the shortcomings of conventional techniques. This object is achieved according to one embodiment of the present invention by providing a magnetic coupling assembly for use in attaching components of a gas flow delivery system to one another. The magnetic coupling assembly of the present invention includes a first member having a first portion and a second member having a second portion. The first member is adapted to be coupled to the second member such that the first portion is adjacent the second portion. A first plurality of magnetic elements are disposed on the first member such that each magnet element has a first pole proximate to the first portion. The first pole of a magnetic element is opposite that of an adjacent magnetic element so that the polarity of the first plurality of magnet elements alternates from one magnetic element to the next along the first portion of the first member. A second plurality of magnetic elements are disposed on the second member such that each magnet element has a first pole proximate to the second portion. The first pole of each magnetic element in the second plurality of magnetic elements t is opposite that of an adjacent magnetic element. This configuration allows the first member to be joined to the second member by the magnetic attraction between the first plurality of magnetic elements and the second plurality of magnetic elements. It also allows the first member to be separated from the second member simply by rotating the first member relative to the second member.

It is yet another object of the present invention to provide a system for delivering a breathing gas to a user that includes such a magnetic coupling assembly, and to provide a method of coupling components of a gas flow delivery system using the a magnetic coupling assembly.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
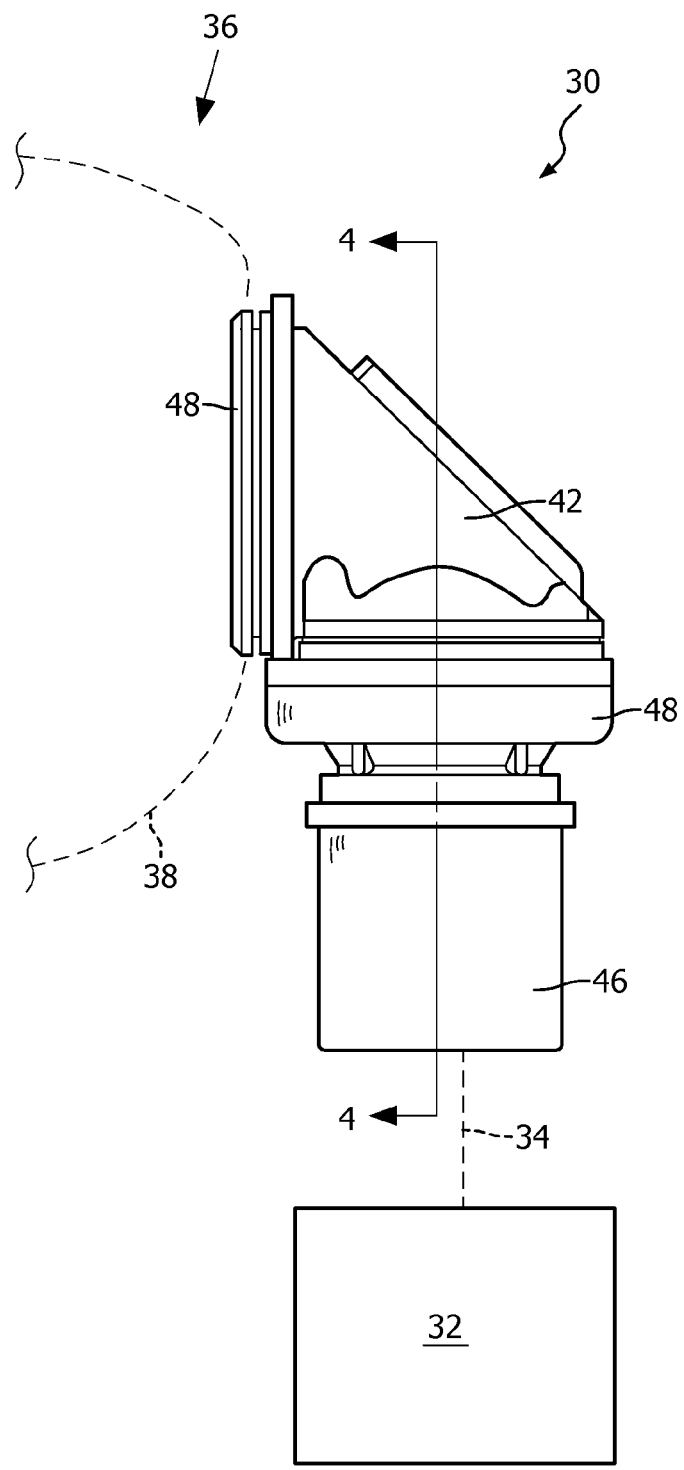
FIG. 1 is a side view of a coupling member that includes a first embodiment of a magnetic coupling assembly according to the principles of the present invention, and also schematically illustrates the components of a pressure support system utilizing the coupling member.

Referring now to FIG. 1, a gas flow delivery system 30 for delivering a flow of gas to an airway of a patient using a magnetic coupling assembly according to the principles of the present invention is illustrated. Gas flow delivery system 30 comprises a pressure/flow generating device 32 that produces a flow of gas. A conduit assembly 34 is coupled to an outlet of the flow/pressure generating device to communicate a flow of gas from the pressure/flow generating device to the user.

Pressure/flow generating device 32 is any conventional ventilator, pressure support system, or other device that is used to communicate a flow of gas or gas at an elevated pressure above the ambient pressure to the airway of the user. Examples of such systems include, but are not limited to: a ventilator, continuous positive airway pressure (CPAP) device, or a variable pressure device, e.g. an auto-titrating device, proportional assist ventilation (PAV®) device, proportional positive airway pressure (PPAP®) device, C-Flex™ device, Bi-Flex™ device, or a BiPAP® device manufactured and distributed by Respironics, Inc. of Pittsburgh, Pa., in which the pressure provided to the patient varies with the patient's respiratory cycle so that a higher pressure is delivered during inspiration than during expiration, or other pressure support device. Other devices that communicate a flow of gas with an airway of a patient suitable for use in with the present invention include devices that apply a high and low or positive and negative pressure to the airway for purposes of secretion clearance or loosening.

A patient interface assembly 36, which typically includes a interface device 38 (such as a mask), a headgear assembly 40 (see FIG. 10), and a conduit coupling 42, is coupled to the distal end portion of conduit assembly 34. The present invention contemplates that patient interface device 38 is any device adapted to communicate the flow of gas from the patient circuit to the airway of the user, such as a nasal mask that seals around the patient's nares. Examples of other patient interface devices include, but are not limited to, nasal pillows or prong that insert or seal each nare, a nasal/oral mask, a full face or total mask, a hood, a tracheal tube, an endotracheal tube. Conduit coupling 42 is typically an elbow that is rotatably coupled to the shell of the mask. However, the present invention contemplates that the conduit coupling can have any other configuration or can be omitted entirely. In which case, the end of the conduit is coupled directly to the mask.

It is to be further understood that various components may be provided in or coupled to pressure/flow generating device 32, conduit assembly 34, patient interface assembly 36, or any combination thereof. For example, a bacteria filter, pressure control valve, flow control valve, pressure/flow/temperature/humidity sensor(s), meter, pressure filter, humidifier, and/or heater can be provided in or attached to the patient circuit.

Figure 3:
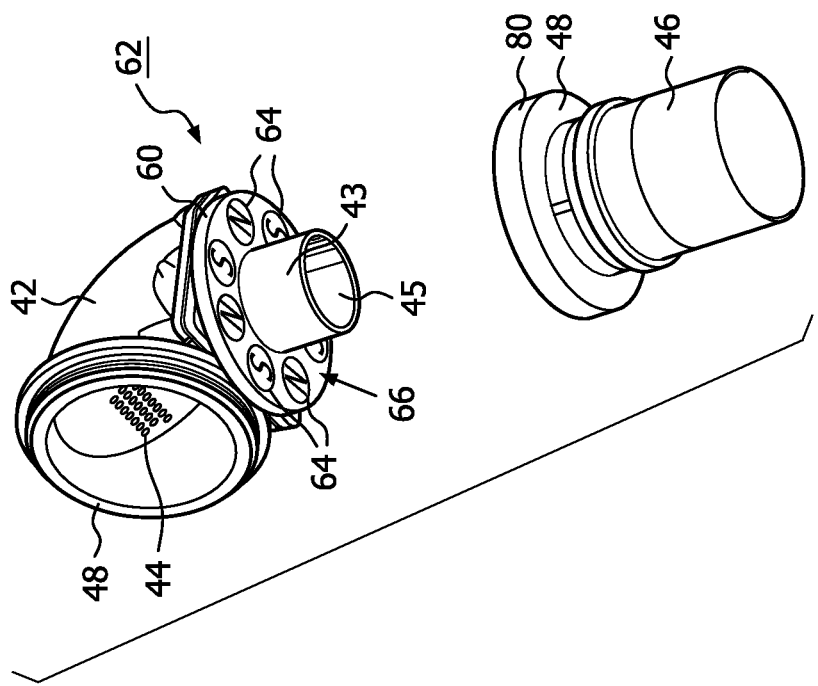
FIGS. 2 and 3 are exploded perspective top and bottom views, respectively, of the coupling member of FIG. 1.
Figure 4:
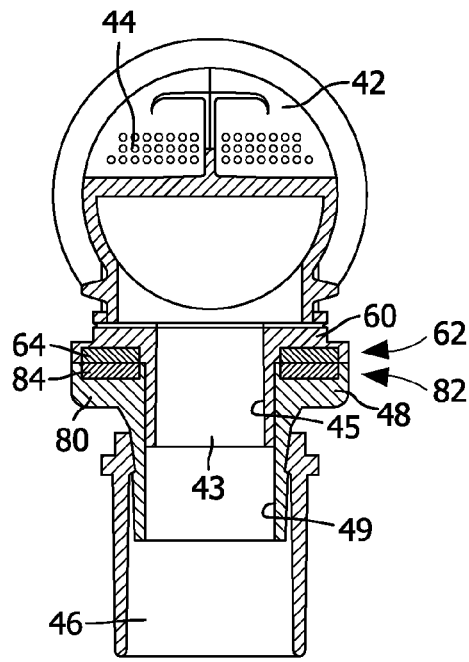
FIG. 4 is a cross-sectional view of the coupling member taken along line 4-4 of FIG. 1.

Gas flow delivery system 30 shown in FIG. 1 is a single-limb system, meaning that the conduit assembly 34 includes only one gas delivery conduit, which is also referred to as a patient circuit or air hose, connecting the patient to the pressure/flow generating device. In a single-limb system, an exhaust assembly 44 (see FIGS. 3 and 4) is provided in the patient circuit for venting gases, such as the patient's exhaled gases, from the system. The exhaust assembly can be provided on the patient interface assembly and/or on the patient circuit and can have a wide variety of configurations depending on the desired manner in which gas is to be vented from the pressure support system. In the exemplary embodiment illustrated in FIGS. 3 and 4, the exhaust assembly comprises a plurality of vent holed defined through conduit coupling 44.

The present invention also contemplates that the gas flow generating system can be a two-limb system, which includes a delivery conduit and an exhaust conduit operatively connected to the airway of the patient. A key difference between a single-limb system and a two-limb system is that in a two-limb system, there is an exhaust conduit that carries exhaust gas from the patient. An exhaust valve is also typically provided at the end of the exhaust conduit distal from the patient. The exhaust valve is normally actively controlled to maintain a desired level of pressure in the system, which is commonly known as positive end expiratory pressure (PEEP). This is accomplished by controlling the flow of exhaust gas from the otherwise closed system.

In the illustrated exemplary embodiment an end connector 46 is shown that couples to the patient circuit so that end connector defines a portion of the conduit assembly. This configuration allows the major portion of conduit assembly 34 to be any existing or conventional tubing; typically a flexible hose with friction couplings at each end. Assembling the air hose to the end connector merely involves attaching the friction fitting to the cylindrical portion of end connector 46.

End connector 46 is coupled to a first collar 48, which includes a flange having a central opening 49 that defines a portion of the gas flow passage. In an exemplary embodiment, the connection between end connector 46 and first collar 48 is a rotatable coupling so that the end connector (and the air hose attached thereto) can rotate with respect to first collar 48. Any suitable technique can be used to rotatably attached first collar 48 to end connector 46. Such a rotatable connection between these components of the gas flow delivery system present torque in the form of twisting of the air hose from being transferred to the patient interface assembly. The present invention also contemplates providing a rigid (non-rotatable) connection between end connector 46 and first collar 48. The present invention even further contemplates eliminating end connector 46 entirely so that first collar 48 is coupled directly to the end of the air hose or defines the end of the air hose.

Although a generally tubular configuration has been illustrated for first collar 48 and end connector 46, the present invention contemplates that the one or both of these components can have any other shape, e.g., non-cylindrical, so long as it accomplishes the function of carrying a flow of fluid from one place to another.

In an exemplary embodiment of the present invention, patient interface device 38 is rotatably attached to conduit coupling 42. This is accomplished using any conventional attachment technique. For example, the present invention contemplates attaching a connecting portion 48 of the conduit coupling to a mask shell 50 (see FIG. 10). Conduit coupling 42 includes an extension 43 that inserted into central opening 49. A central opening 45 is provided in extension 43 to define a portion of the gas flow passage.

As noted above, a magnetic coupling assembly is used to couple the various components of the gas flow delivery system to one another. In the embodiment illustrated in FIGS. 1-4, the magnetic coupling assembly couples patient interface assembly 36 to conduit assembly 34. More specifically, the magnetic coupling assembly joins conduit coupling 42 in the patient interface assembly to first collar 48 in the conduit assembly.

The magnetic coupling assembly according to the principles of the present invention includes a first member 60, which is in the form of a second collar, and a second member 80 that couple to one another. In the illustrated embodiment, second member 80 corresponds to first collar 48. A first plurality of magnetic elements, generally indicated at 62, are disposed on first member 60 and a second plurality of magnetic elements, generally indicated at 82, disposed on the second member.

In the embodiment illustrated in FIGS. 1-4, first plurality of magnetic elements 62 includes a number of individual magnetic elements 64, each of which is disposed on the first member such that a first pole, labeled North (N) or South (S), is disposed proximate to an exposed portion or surface 66 of first member 60. Similarly, second plurality of magnetic elements 82 includes a number of individual magnetic elements 84, each of which is disposed on the second member such that a first pole, labeled North (N) or South (S), is proximate to an exposed portion or surface 86 of second member 80. As a result, each magnetic element in the first and second plurality of magnetic elements will have a second pole that is spaced apart from the exposed portion of the first or second member. The first plurality of magnetic elements and the second plurality of magnetic elements are arrayed on the first and second members, respectively, such that the same number of individual magnetic elements having substantially the same shape are provided in each group of magnetic elements. This allows the magnetic elements in first group 62 to mate with the magnetic elements in second group 82 in a substantial alignment with each other. In the illustrated embodiment, the first plurality of magnetic elements and the second plurality of magnetic elements are also arrayed on the first and second members, respectively, such that the magnetic element are disposed around openings 45 and 49.

The first plurality of magnetic elements are disposed on the first member such that the pole of each magnetic element in the first plurality of magnetic elements is opposite that of an adjacent magnetic element. That is, the adjacent magnetic elements present different poles at the exposed surface. So that along the array of magnetic elements, e.g., in the clockwise or counter-clockwise direction around the central opening (45, 49), i.e., along the circumference of the first or second member, the pole of the magnetic elements at the exposed surface alternates North, South, North, South, and so on.

By providing the magnetic elements in this type of array, the two components of the gas delivery system couple together using the magnetic attraction between the magnetic elements in the first and second groups of magnetic elements. It can be appreciated that the strength of the connection is related to the strength of the magnetic fields, which is determined, for example, by the number of magnetic elements used in each group.

To connect first member 60 to second member 80, these two components need only be moved toward each other. The magnetic field generated between the two magnetic arrays (i.e., first and second plurality of magnetic elements 62 and 82) will pull them together. As the first member and the second member approach each other, the individual magnetic elements in the first member will align with the individual magnetic elements in the second member having an opposite pole. In this manner, the arrays of magnetic elements will force the two components to join in such a way such that the magnetic elements in the first group match up with magnetic elements in the second having opposite poles. As a result, the first member, i.e., conduit coupling 62, will self-align with the second member, i.e., collar 48. Based on the number of magnetic elements used in the groups, there will be a limited number of angular positions that the first member can assume relative to the second member.

Figure 2:
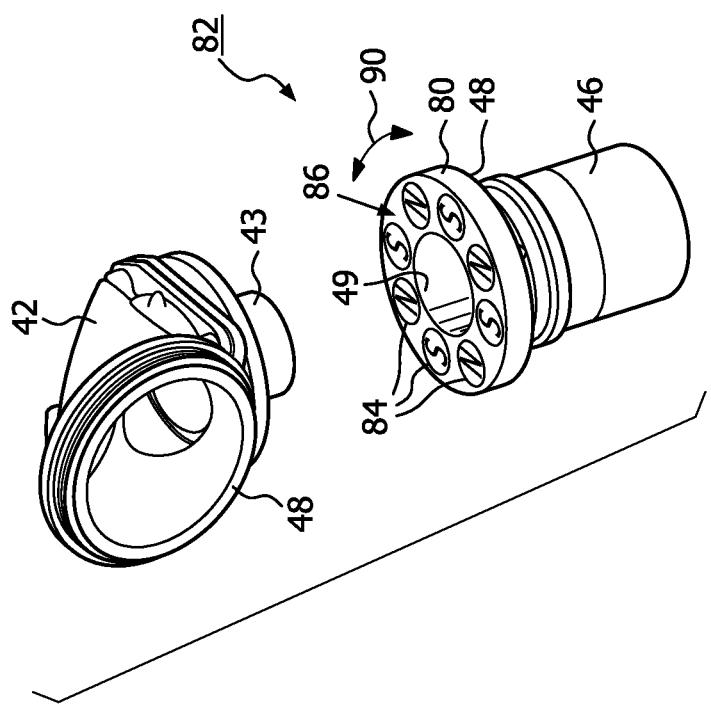

To detach first member 60 from second member 80 the user need only twist or rotate the first member relative to the second member in either direction, as indicated by arrow 90 in FIG. 2. This will cause the poles of the magnetic elements to become unaligned, thereby reducing the magnetic attraction between first group 62 and second group 82 of magnetic elements. Continued rotation of the first member relative to the second member will cause the magnetic element having the same pole to approach each other. This will result in a repulsive force being generated between the first plurality of magnetic elements and the second plurality of magnetic elements. This repulsive force will increase in accordance with the inverse square law as the like-pole magnetic elements in each group approach their counterpart in the other group of magnetic elements. As a result, the first member will be pushed or forced away from the second member thereby detaching these two elements.

Figure 5:
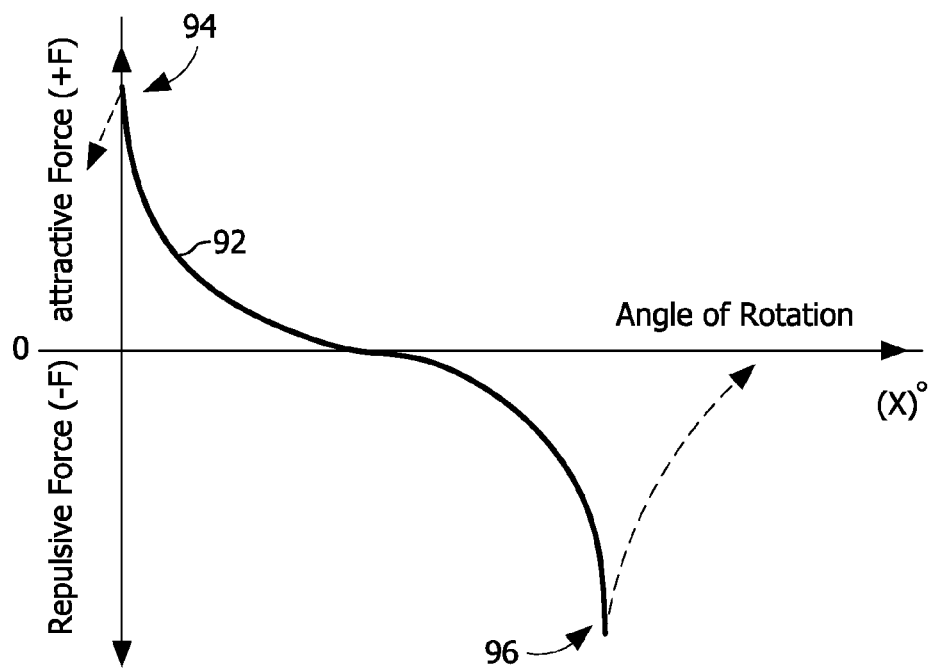
FIG. 5 is a graph illustrating how the attractive and repulsive forces between the magnetic elements in the magnetic coupling assembly vary as the components of the magnetic coupling assembly are rotated relative to one another.

FIG. 5 graphically illustrates how the attractive force (F) and repulsive force (−F) between the first member and the second member, i.e., between the first plurality of magnetic elements and the second plurality of magnetic elements changes based on the angular position or angle of rotation between the members or elements. Please note that this graph is meant for illustration only. Line 92 illustrates the relationship between the angular position of the first member relative to the second member the and magnetic attraction or repulsion therebetween. Point 94 corresponds to the point of maximum attraction, which be the angular position in which the magnetic elements in the first group of magnetic elements 62 are aligned with an opposite pole magnetic element in the second group or magnetic elements 82. When the first member and the second member are coupled, they will naturally and automatically adjust their angular position relative to each other to seek this point. On the other hand, point 96 corresponds to the point of maximum repulsion, which be the angular position in which the magnetic elements in the first group of magnetic elements 62 are aligned with the same pole magnetic element in the second group or magnetic elements 82.

In the illustrated embodiment, magnetic elements 64 and 84 are embedded in a symmetrical pattern about central openings 45, 49, with each magnetic element being approximately the same size and shape. It is to be understood that the present invention contemplates providing the groups of magnetic elements, and the individual magnet elements in each group, in a variety of shapes, sizes, patterns, and configurations. The present invention also contemplates that the first and second member on which the magnetic elements are located can also have different configurations. FIGS. 6A-10B are provided to show various alternative configurations for the magnetic elements and the first an second members.

Figure 6A:
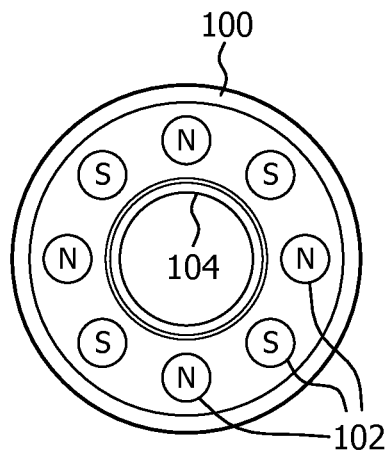
FIGS. 6A and 6B are top and cross-sectional views, respectively, of a first member in a second embodiment of a magnetic coupling assembly according to the principles of the present invention.
Figure 7A:
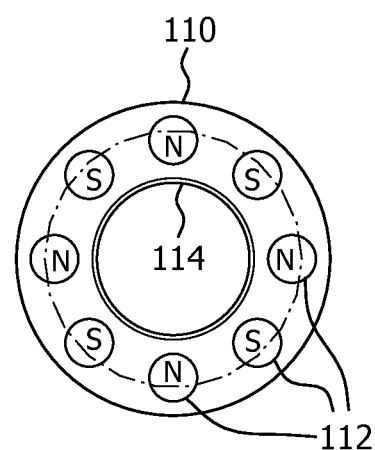
FIGS. 7A and 7B are bottom and cross-sectional views, respectively, of a second member in the second embodiment of a magnetic coupling assembly according to the principles of the present invention.
Figure 6B:
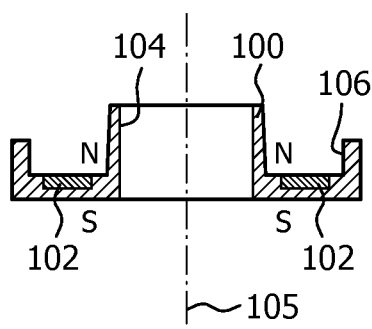
Figure 7B:
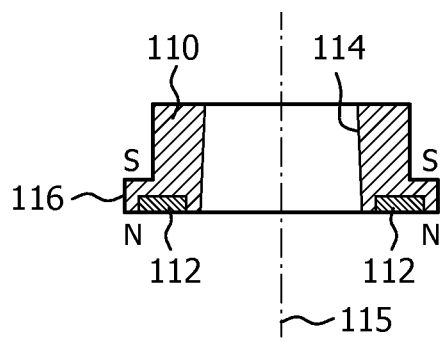

FIGS. 6A and 6B illustrate a second embodiment the portion of the magnetic coupling assembly that is operatively coupled to the conduit assembly, and FIGS. 7A and 7B illustrate a second embodiment the portion of the magnetic coupling assembly that is operatively coupled to the patient interface assembly. In this embodiment, a first member 100 includes eight generally circular magnetic elements 102 disposed in a symmetrical pattern around central opening 104. A second member 110 also includes eight generally circular magnetic elements 112 disposed in a symmetrical pattern around central opening 114. As shown in this embodiment, first member 104 includes a channel 106 adapted to receive a rim or flange 116 provided on second member 110. The present invention contemplates engaging the rim of second member 110 with the wall or walls of the channel in first member 100 to enhance the attachment of the first member to the second member.

It should also be noted that FIGS. 6B and 7B illustrate an exemplary arrangement for the magnetic elements on the first and second members. As shown in these figures, each magnetic element 102 or 112 is embedded in a portion of the first or second member such that surface of each magnetic element is exposed and substantially flush with an adjacent surface of the member in which the magnetic is embedded. This provides a tight or flush surface-to-surface engagement between the first and second members when these two components are coupled, thereby minimizing gas leaks at the junction between these components. Of course, other gas leak reduction techniques or components, such as O-rings and gaskets can be provided to further reduce gas leaks. For example, a gasket can be provided that overlies the magnetic elements on or both of the first and second members.

FIGS. 6B and 7B also provide a clear illustration of one possible arrangement of the magnetic poles of each magnetic element—with one pole being proximate to the surface or first portion of the first or second member and the other, opposite pole being spaced apart from the surface or first portion of the first or second member. In other words, the magnetic poles (N and S) of each magnetic element are aligned such that a line passing between both poles in the same magnetic element is generally parallel to an axis 105 of the first member for the magnetic elements in the first member or to an axis 115 of the second member for the magnetic elements in the second member. Axis 105 and 115 correspond the gas pathway through the first or second member.

Figures 8A, 8B:
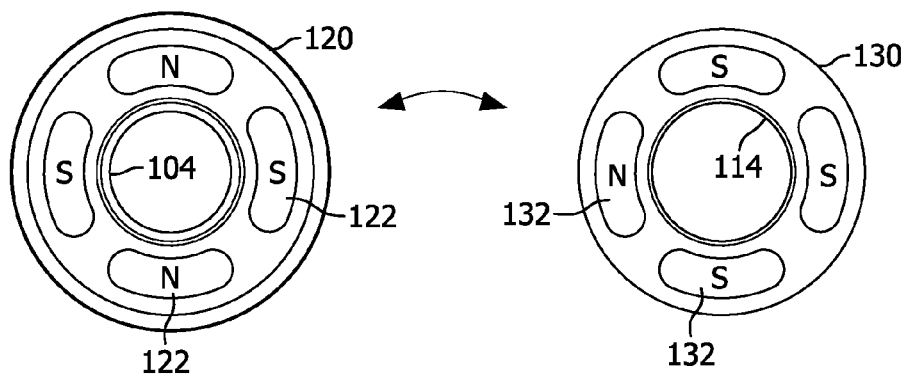
FIGS. 8A and 8B are top and bottom views, respectively, of first and second members in a third embodiment of a magnetic coupling assembly according to the principles of the present invention.

FIGS. 8A and 8B illustrate a third embodiment of a first member 120 and a second member 130 in the magnetic coupling assembly of the present invention. It should be noted that either the first member or the second member can be attached to the air hose or the patient interface assembly. In this embodiment, first and second members 120 and 130 include only four magnetic elements 122, 132 provided in an array around a central opening 104, 124. The magnetic elements have an irregular shape, such as a kidney, elliptical, or oval shape. It can be appreciated that the number of magnetic elements and the specific configuration for each element, as well as their positioning and distribution on the first and second members, can be varied greatly while keeping within the spirit of the present invention.

Figures 9A, 9B:
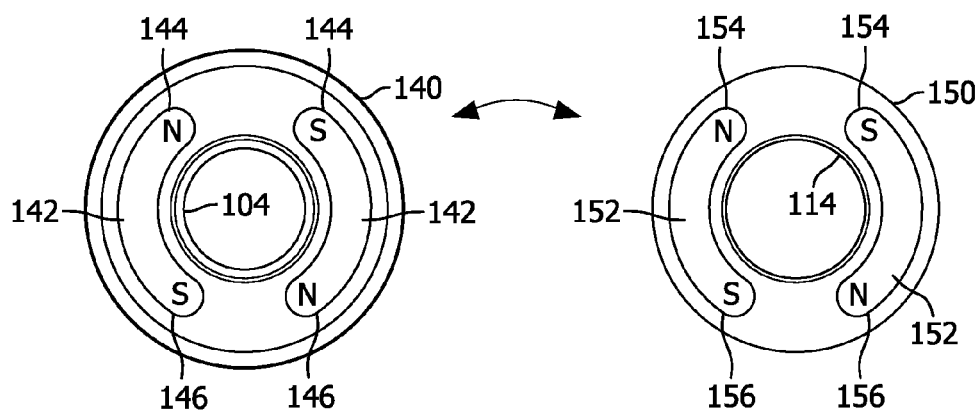
FIGS. 9A and 9B are top and bottom views, respectively, of first and second members in a fourth embodiment of a magnetic coupling assembly according to the principles of the present invention.

FIGS. 9A and 9B illustrate a fourth embodiment of a first member 140 and a second member 150 in the magnetic coupling assembly of the present invention, where either of these members can be operatively coupled to the conduit assembly or the patient interface assembly. First member 140 includes only two magnetic elements 142, and second member also includes only two magnetic elements 152. One difference between this embodiment and the previous embodiment has to do with the orientation of the poles of the magnetic elements. In the previous embodiments, the poles (N and S) of each magnetic element are aligned with axis 105 and 115 (see FIGS. 6B and 7B). In addition, in the previous embodiment, the plurality of magnetic elements on each member were defined by individual magnetic elements. In this embodiment, however, the magnetic elements are oriented on each member such that the magnetic poles 144, 146 and 154 and 156 of each magnetic element lie in generally the same plane. In addition, the plurality of magnetic elements disposed on the first member and are defined by separate portions, i.e., separate poles of a common magnetic element. Likewise, the plurality of magnetic elements disposed on the second member and are defined by separate portions, i.e., separate poles of a common magnetic element.

Figures 10A, 10B:
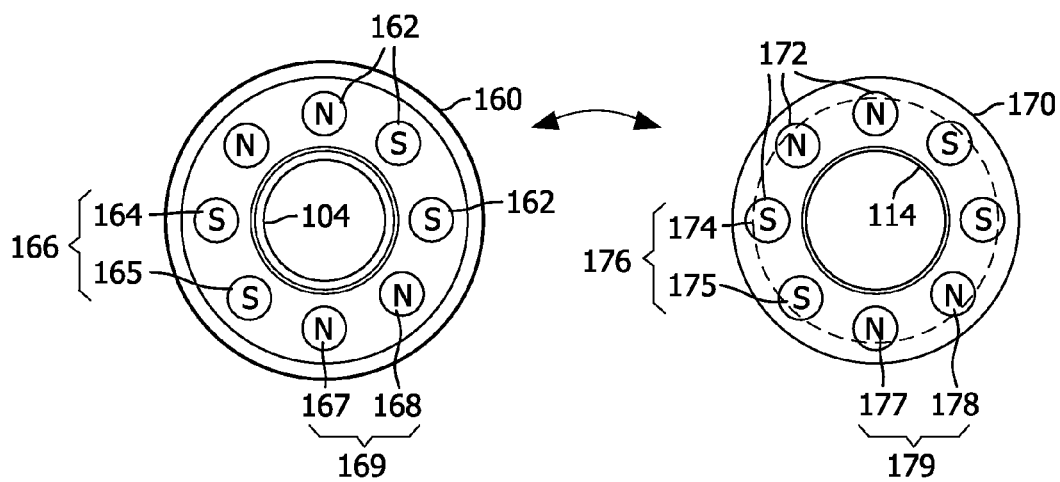
FIGS. 10A and 10B are top and bottom views, respectively, of first and second members in a fifth embodiment of a magnetic coupling assembly according to the principles of the present invention.

FIGS. 10A and 10B illustrate a fifth embodiment of a first member 160 and a second member 170 in the magnetic coupling assembly of the present invention. As before, either of these members can be coupled to the conduit assembly or the patient interface assembly. In this embodiment, magnetic elements 162 and 172 are disposed on the first member and second member, respectively, such that each magnetic element in the same plurality of magnetic elements is not necessarily presenting a different pole that than that of an adjacent magnetic element. In other words, in the previous embodiment, the magnetic poles are arranged in the North, South, North, South alternating pattern about the central opening. In the embodiment of FIGS. 10A and 10B, the poles are arranged in a North, North, South, South, . . . pattern about central opening 104 and 114.

This embodiment still provides alternating poles about the central opening when it is considered that each pair of like-pole magnetic elements defines a single magnetic element in the plurality of magnetic elements disposed on the first member or the second member. That, is magnetic elements 164 and 165 define a first magnetic element 166, and magnetic elements 167 and 168 define a second magnetic element 169. First magnetic element 166 and second magnetic element 169 define a plurality of magnetic elements disposed on first member 160. Similarly, magnetic elements 174 and 175 define a first magnetic element 176, and magnetic elements 177 and 178 define a second magnetic element 179. First magnetic element 176 and second magnetic element 179 define a plurality of magnetic elements disposed on second member 170.

Figure 11:
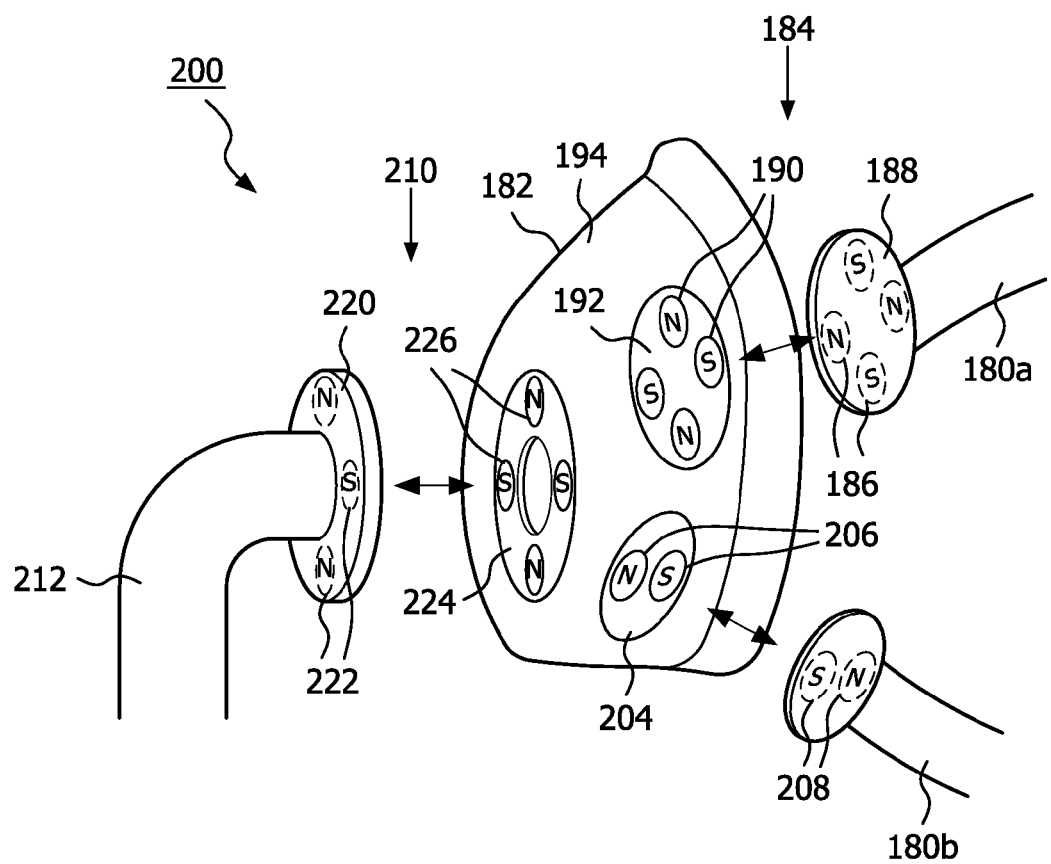
FIG. 11 is an exploded view of a patient interface assembly utilizing the magnetic coupling assembly according to the principles of the present invention.

In the embodiments presented above, the magnetic coupling assembly is used to join portions of the conduit assembly to the patient interface assembly and/or the gas flow/pressure generating device. It is to be understood, however, that the present invention contemplates using the magnetic coupling assembly to join other portions of the pressure support system. FIG. 11 illustrates examples of magnetic coupling assemblies used to join portions of a headgear assembly, such as headgear straps 180*a* and 180*b*, to a patient interface device 182.

More specifically, a first magnetic assembly, generally indicated at 184, is provided to couple headgear strap 180*a* to patient interface device 182. Magnetic assembly 184 includes magnetic elements 186 on an end portion 188 of headgear strap 180*a* and magnetic elements 190 on a first mounting portion 192 provided on a shell 194 of patient interface device 182. A second magnetic assembly, generally at 200, is provided to couple an end portion 202 of headgear strap 180*b* to a second mounting portion 204 on patient interface device 182. In the illustrated embodiment, only two magnetic elements 206 and 208 are provided on mounting portion 204 and end portion 202, respectively.

A third magnetic assembly, generally indicated at 210, is provided to couple a coupling member 212 to patient interface device 182. Third magnetic assembly includes a first member 220 having a first plurality of magnetic elements 222, and a second member 224 having a second plurality of magnetic elements 226

In the illustrated embodiments, the surfaces on which the magnetic elements are disposed, such as surfaces 66 and 86, are shown as being planar surfaces. The present invention also contemplates that these surface can be non-planar.

The magnetic elements of the present invention can be formed from any magnetic material, ferromagnet, or magnetic device. In, addition the magnetic elements can be formed from a permanent magnet or from a device that is selectively magnetized, such as an electro-magnetic device. In the latter case, a power source is needed to energize the electro-magnets in each group of magnetic elements.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for delivering a breathing gas to a user comprising:
   (a) a gas flow/pressure generating device adapted to produce a flow of gas, the gas flow generating device having a housing and an outlet on an exterior of the housing;
   (b) a patient interface assembly adapted to be worn by such a user; and
   (c) a conduit assembly having a first end portion operatively coupled to the outlet of the housing and a second end portion operatively coupled to the patient interface assembly, wherein the conduit assembly carries the flow of gas from the gas flow generating device during operation of the gas flow generating system;
   (d) a magnetic coupling assembly comprising:
      (1) a first member operatively coupled to the second end portion of the conduit assembly, the first member having a channel having a plurality of walls,
      (2) a second member operatively coupled to the patient interface assembly, the second member having a flange, and
      (3) a plurality of magnetic elements disposed on the first member in the channel and the second member on a bottom of the flange such that in an engaged position the flange is received in the channel and engages the walls and the magnetic elements on the first member are attracted to the magnetic elements on the second member and rotating the first member relatively to the second member causes a repulsive force to be generated between the magnetic elements on the first member and the magnetic elements on the second member.

2. The system of claim 1, wherein the plurality of magnetic elements include:
   a first plurality of magnetic elements disposed on the first member such that each magnet element has a first pole proximate to a coupling portion of the first member, and wherein the first pole of a magnetic element in the first plurality of magnetic elements is opposite that of an adjacent magnetic element; and
   a second plurality of magnet elements disposed on the second member such that each magnet element has a first pole proximate to a coupling portion of the second member, and wherein the first pole of a magnetic element in the second plurality of magnetic elements is opposite that of an adjacent magnetic element.

3. The system of claim 1, wherein at least two magnetic elements in the first plurality of magnetic elements are defined by separate portions of a single magnet that is disposed on the first member such that both poles are proximate to a coupling portion of the first member, and wherein at least two magnetic elements in the second plurality of magnetic elements are defined by separate portions of a single magnet that is disposed on the second member such that both poles are proximate to a coupling portion of the second member.

4. The system of claim 1, wherein the plurality of magnetic elements include at least four magnetic elements disposed on the first member and at least four magnetic elements disposed on the second member.

5. The system of claim 1, wherein the first member is a first collar having a first central opening defined therein, wherein the plurality of magnetic elements include a first plurality of magnetic elements disposed around the first central opening, wherein the second member is a second collar having a second central opening defined therein, and wherein the plurality of magnetic elements include a second plurality of magnetic elements disposed around the second central opening.

6. The system of claim 1, further comprising and exhaust assembly associated with the patient interface assembly, the conduit assembly or both.

7. The system of claim 1, further comprising a rotatable coupling provided in the conduit assembly, at a first side of the magnetic coupling assembly that is operatively coupled to the conduit assembly, at a second side of the magnetic coupling assembly that is operatively coupled to the patient interface assembly, or any combination thereof.

8. The system of claim 1, wherein the patient interface assembly comprises:

a shell having a first side and a second side;

a cushion coupled to the first side of the shell; and a coupling member coupled to the second side of the shell, wherein the magnetic coupling assembly is disposed between the coupling member and the conduit assembly and joins the coupling member to the conduit assembly in the engaged position.

9. The system of claim 8, wherein the coupling member is rotatably coupled to the shell.

10. A method of coupling components of a gas flow delivery system comprising:

providing a gas flow/pressure generating device;

providing a patient interface assembly adapted to be worn by such a user, wherein the patient interface assembly includes a conduit coupling portion;

providing a conduit assembly having a first end portion and a second end portion;

coupling the first end portion of the conduit assembly to an outlet of the gas flow/pressure generating device; and coupling the second end portion of the conduit assembly to the patient interface assembly using a magnetic coupling assembly comprising: (1) a first member having a channel having a plurality of walls, (2) a second member having a flange, and (3) a plurality of magnetic elements disposed on the first member in the channel and the second member on a bottom of the flange, wherein the coupling the second end portion of the conduit assembly to the patient interface assembly comprises inserting the flange in the channel and engaging the walls and magnetically attracting the magnetic elements on the first member to the magnetic elements on the second member.

11. The method of claim 10, further comprising detaching the second end portion of the conduit assembly from the patient interface assembly by rotating the second end portion of the conduit assembly relative to the patient interface assembly such that a repulsive force is generated between the magnetic elements on the first member and the magnetic elements on the second member.

12. A method of coupling components of a gas flow delivery system comprising:

providing a gas flow/pressure generating device;

providing a patient interface assembly adapted to be worn by such a user, wherein the patient interface assembly includes a conduit coupling portion having a first plurality of magnetic elements disposed thereon;

proving a conduit assembly having a first end portion and a second end portion, wherein the second end portion includes a second plurality of magnetic elements disposed thereon;

coupling the first end portion of the conduit assembly to an outlet of the gas flow/pressure generating device; and coupling the second end portion of the conduit assembly to the patient interface assembly by magnetically attracting the first plurality of magnetic elements to the second plurality of magnetic elements, wherein the patient interface assembly includes a patient interface device having a third plurality of magnetic elements disposed thereon and a headgear device having a fourth plurality of magnetic elements disposed thereon, the method further comprising coupling the patient interface device to the headgear device by magnetically attracting the third plurality of magnetic elements to the fourth plurality of magnetic elements.

13. The method of claim 12, further comprising detaching the patient interface device from the headgear device by rotating the patient interface device relative to the headgear device such that a repulsive force is generated between the third plurality of magnetic elements and the fourth plurality of magnetic elements.

14. The system of claim 1, wherein the patient interface assembly includes a patient interface device having a second plurality of magnetic elements disposed thereon and a headgear device having a third plurality of magnetic elements disposed thereon, wherein the patient interface device is structured to be coupled to the headgear device by magnetically attracting the second plurality of magnetic elements to the third plurality of magnetic elements.

15. The method of claim 10, wherein the patient interface assembly includes a patient interface device having a second plurality of magnetic elements disposed thereon and a headgear device having a third plurality of magnetic elements disposed thereon, the method further comprising coupling the patient interface device to the headgear device by magnetically attracting the second plurality of magnetic elements to the third plurality of magnetic elements.

* * * * *